United States Patent [19]
Machida et al.

[11] Patent Number: 5,591,120
[45] Date of Patent: Jan. 7, 1997

[54] JOINT CONSTRUCTION FOR ANGLE SECTION OF ENDOSCOPIC INSERTION ROD

[75] Inventors: Mitunori Machida; Mituo Kondo, both of Omiya, Japan

[73] Assignee: Fuji Photo Optical Co., Ltd., Omiya, Japan

[21] Appl. No.: 564,555

[22] Filed: Nov. 21, 1995

[30]  Foreign Application Priority Data

Nov. 25, 1994  [JP]  Japan ................................... 6-314293

[51] Int. Cl.$^6$ ................................................... A61B 1/00
[52] U.S. Cl. .......................... 600/140; 600/139; 600/920; 138/120; 138/155
[58] Field of Search ..................... 600/101, 133, 600/139, 140, 141, 142, 143, 144, 920; 138/120, 155

[56]  References Cited

U.S. PATENT DOCUMENTS

4,805,596  2/1989  Hatori ....................................... 600/139
4,807,598  2/1989  Hasegawa ................................ 600/140
5,052,445  10/1991 Berchem .................................. 138/155
5,217,002  6/1993  Katsurada et al. ...................... 600/139
5,281,454  1/1994  Hanson .................................... 138/155 X

Primary Examiner—Richard J. Apley
Assistant Examiner—Beverly M. Flanagan
Attorney, Agent, or Firm—Oblon, Spivak, McClelland, Maier & Neustadt, P.C.

[57]  ABSTRACT

A joint construction for connecting a flexibly bendable angle section of an endoscopic insertion rod with an anteriorly and/or posteriorly located section of the insertion rod, including a line-wrapping layer formed on a fore end portion of a resilient outer skin layer of the angle section at a joint with the adjoining section, and a rigid cover ring fitted on the line-wrapping layer for protective purposes. The rigid cover ring is externally tapered or gradually thinned down in its front and rear end portions to provide front and rear bevel surfaces. The rear bevel surface of the rigid cover ring is embedded under an annular fin which is formed in and out of a resilient skin layer at a position bordering on outer edges of the rear bevel surface, precluding possibilities of rear edges of the rigid cover ring hitting against a sharp-edged fore end of a tubular sheath member of a trocar particularly at the time of extraction of the endoscopic insertion rod from the trocar, and ensuring smooth retraction and protrusion of the endoscopic insertion rod into and out of a trocar.

5 Claims, 5 Drawing Sheets

JOINT CONSTRUCTION FOR ANGLE SECTION OF ENDOSCOPIC INSERTION ROD

BACKGROUND OF THE INVENTION

1. Field of the Art

This invention relates to endoscopes which are in wide use in medical fields for intracavitary observations in diagnostic or therapeutic treatments, and more particularly to a joint construction for connecting an angle section of an endoscopic insertion rod between anterior and posterior sections of the insertion rod.

2. Prior Art

Generally, endoscopes largely consist of a rod-like insertion member and a manipulating head assembly which is connected to the proximal end of the rod-like insertion member (hereinafter referred to simply as "insertion rod" for brevity). Depending upon the rigidity of the insertion rod, endoscopes can be classified into a hard type with a hard insertion rod which has a rigid body over its entire length, and a soft or flexible type with a flexible insertion rod which has a soft and flexible body substantially over its entire length except an angle section and a rigid tip end section which are successively connected to the fore end of the flexible body. Flexible endoscopes are introduced into the body of patient by oral insertion, while hard endoscopes are normally introduced by percutaneous insertion through a percutaneously perforated hole as in the case of peritoneoscopes. Even a hard endoscope, which is likewise provided with an illumination window and an endoscopic observation window at the distal end of the insertion rod, needs to be able to secure a broad view field within an intracavitary portion under observation or to be able to give a therapeutic treatment on a particular region of interest. In this regard, it has been known in the art to provide a flexibly bendable angle section between a fore end of a main body of an insertion rod section in the form of a rigid pipe and a rigid tip end section which accommodates endoscopic observation means at the distal end of the insertion rod, thereby to turn the rigid tip end section into a desired direction by remote-controlling the angle section from a manipulating head assembly of an endoscope.

Figure 5:
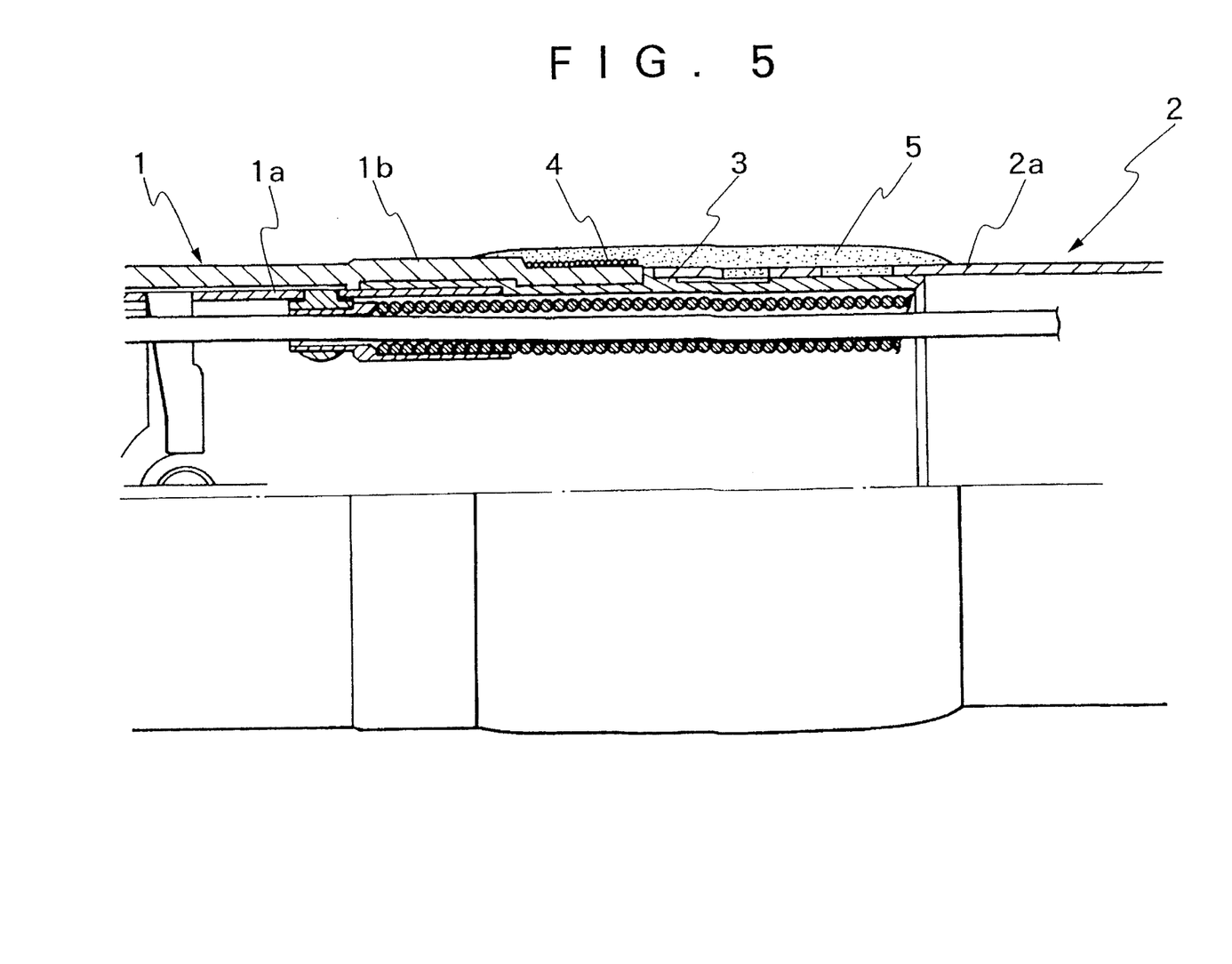
FIG. 5 is a sectional view of a conventional joint construction connecting an angle section with a main endoscopic insertion section of an endoscopic insertion rod.

In most cases, the angle section is constituted by a series of flexibly connected angle rings and a resilient outer skin layer of a net or of a flexible synthetic resin material which is fitted around the angle rings. The outermost angle rings at the opposite ends of the angle section are connected to the insertion rod section and the rigid tip end section, respectively. In this regard, as shown in FIG. 5, for example, at the joint of an angle section 1 with an insertion rod section 2, an angle ring 1a at the proximal end of the angle section 1 is securely fixed to a tubular main body 2a of the insertion rod section 2 by soldering or other suitable fixation means through a joint ring 3. An outer skin layer 1b of the angle section 1 is fixed on the joint ring 3 by a line-wrapping layer 4, which is in turn anchored in position by an adhesive 5.

However, in case of an endoscope to be introduced into the body percutaneously as in the case of a peritoneoscope, it has been the general practice to use a so-called trocar as a guide means which provides a path of insertion for the endoscope. As well known in the art, trocars of this sort are constituted by an outer tubular sheath member and an inner sharp-pointed perforator needle which is extractably fitted into the outer sheath member. The outer sheath member is tapered off at its fore end into a sharp blade-like shape in section to eliminate radially stepped portions around the circumference of the perforator needle in assembled state. In order to introduce an insertion rod of an endoscope into an abdominal cavity under the guidance of a trocar of this sort, firstly the perforator needle is set in a fully inserted position within the outer sheath member, with its sharp-pointed end protruded out of the sharp-edged fore end of the outer sheath member. Then, the trocar is introduced into the body of patient, piercing through outer skin layers with the sharp-pointed end of the perforator needle, for example, toward a region of particular interest within an abdominal cavity. Thereafter, the inner perforator needle is extracted from the outer sheath member, and, in place of the perforator needle, an insertion rod of an endoscope is fitted into the outer sheath member of the trocar, protruding a fore end portion of the insertion rod into the intracavitary region of interest. At the time of an endoscopic examination, the intracavitary portion under observation is normally inflated with a pneumoperitoneum gas for the purpose of broadening the view field of the endoscope and at the same time for precluding bruises or other damages to intracavitary wall surfaces. In such a case, it becomes necessary to prevent the pneumoperitoneum gas from leaking to the outside through a clearance between the insertion rod of the endoscope and the outer sheath member of the trocar. This problem has thus far been coped with by tightly fitting the insertion rod in the outer sheath member of the trocar, that is, by minimizing the dimensional difference between the outside diameter of the insertion rod and the inside diameter of the outer sheath member.

Figure 6:
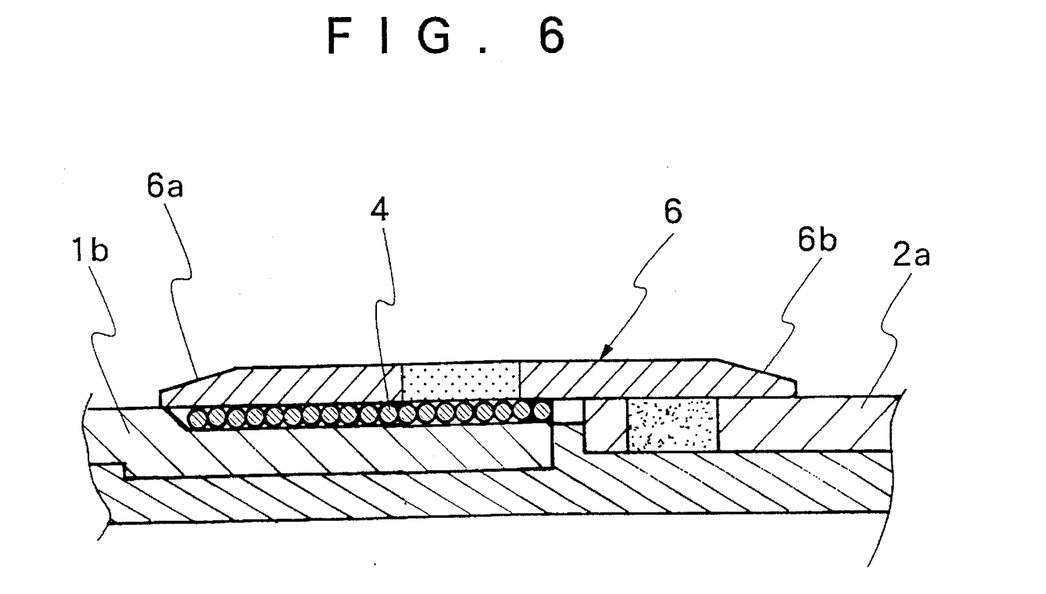
FIG. 6 is a sectional view of another conventional joint construction similarly connecting an angle section with a main endoscopic insertion section.

However, when an endoscopic insertion rod is tightly fitted in an outer sheath member which is thinned down toward its fore end in the fashion of a sharp knife blade, it is very likely that the adhesive agent, which anchors line-wrapping layers at the joints of the angle section with main body structures of the rigid tip end section and the insertion rod section of the endoscope, be scraped off by the sharp-edged fore end of the outer sheath member, leaving scraped crumbles of the adhesive in the body as the insertion rod of the endoscope is moved back and forth within the outer sheath member. As a countermeasure to this problem, it has also been known in the art to employ a rigid cover ring 6 of a metallic material as a substitute for the above-described adhesive agent, thereby covering the line-wrapping layer 4 at a joint portion as shown in FIG. 6. The rigid cover ring 6 is externally gradually thinned down in and toward its opposite end portions, so that the insertion rod presents a streamlined profile across the cover ring 6, free of radially stepped surfaces.

For receiving an insertion rod with such a rigid cover ring, it is necessary for the trocar sheath member to be able to ride over the rigid cover ring smoothly as the insertion rod is moved back and forth therein. The rigid cover ring is usually fitted on a resilient protective cover tube of a synthetic resin material, which forms an outer skin layer on a body of a joining section or sections of the insertion rod. Therefore, even if the rigid cover ring is thinned down to bring its opposite ends gradually into the level of an underlying resilient skin layer of the insertion rod as smoothly as possible, the end faces of the rigid cover ring tend to stick out radially outward of the underlying resilient skin layer partly due to a discontinuity in rigidity from the rigid cover ring to the resilient outer skin layer and partly due to repeated bending operations of the angle section during use over an extended period of time. If the rigid cover ring sticks out radially outward of the resilient outer skin layer, even in a very slight degree, difficulties are encountered in moving the endoscopic insertion rod back and forth within the outer sheath member, particularly, at the time of extracting the insertion rod out of the trocar, because in that state the sharp-edged fore end of the outer sheath easily comes into abutment against the proximal end face of the rigid cover ring, hindering its retraction into the outer sheath member of the trocar.

SUMMARY OF THE INVENTION

In order to solve the above-discussed problems of the prior art, the present invention has as its object the provision of a joint-construction for connecting an angle section of an endoscopic insertion rod to an anterior and/or a posterior section of the insertion rod, with a rigid cover ring fitted around a line-wrapping layer at a joint of the angle section with a rigid body of an anterior or posterior insertion rod section in such a manner as to ensure smooth passages of the joint portion into and out of a sharp-edged fore end of an outer sheath member of a trocar.

In accordance with the present invention, there is provided a joint construction for connecting an angle section of an endoscopic insertion rod to an anteriorly or posteriorly adjoining section of the endoscopic insertion rod, including a line-wrapping layer tightly fastening an end of a resilient outer skin layer of the angle section against an underlying rigid structure at a joint with the adjoining section of the insertion rod, and a rigid cover ring fixedly fitted on the line-wrapping layer for protection thereof, characterized in that the joint construction includes front and rear external bevel surfaces formed at front and rear ends of the rigid cover ring by externally tapering front and rear end portions thereof, and a forwardly tapered annular fin formed in and out of a resilient outer skin layer under the rigid cover ring at a position bordering on outer edges of the rear bevel surface of the rigid cover ring and having an internal bevel surface complementarily to the rear external bevel surface on the rigid cover ring, the internal bevel surface of the annular fin being securely bonded on the rear external bevel surface of the rigid cover ring, embedding the rear external bevel surface of the rigid cover ring under the resilient outer skin layer.

The above-described joint construction can be used at both of the front and rear ends of the angle section, which are to be connected to a rigid tip end section and a main insertion rod section, as long as the rear end of a cover ring is located to sit on a resilient outer skin layer with possibilities of abutment against a sharp-edged fore end of a trocar sheath member. In case it is used for joining the angle section with a rigid body of the rigid tip end section or of the main insertion rod section, the rigid cover ring can be retained in a receded position on the rigid body of the joining section while forming a line-wrapping layer on an end portion of the outer skin layer of the angle section, and then slid into position on the line-wrapping layer. By so doing, the rigid cover ring can be securely fixed in position on the line-wrapping layer, in some cases without necessitating application of an adhesive agent for its fixation.

The outer skin layer is formed of a soft resilient material, so that, in case a rigid cover ring is simply fitted tightly on the skin layer of such nature, the edges of the rigid cover ring tend to step out radially outward of the resilient skin layer as the angle section is bent for turning the rigid tip end section into a desired direction, mainly due to a discrepancy in behaviors between a rigid part and a resilient flexible part which are joined together. According to the present invention, however, a proximal end portion of the rigid cover ring, which meets a sharp-edged fore end of an outer sheath member of a trocar from the opposite direction, is embedded in an underlying outer skin layer of the insertion rod to keep it out of direct contact with the sharp-edged fore end of the trocar sheath member, which would otherwise tend to abut against the proximal end face of the rigid cover ring to hinder passage of the angle section on the endoscopic insertion rod particularly at the time of extraction from the outer sheath member. Accordingly, the above-described joint construction ensures unobstructed smooth movement of an endoscopic insertion rod into and out of the outer sheath member of a trocar.

The above and other objects, features and advantages of the invention will become apparent from the following particular description of the invention, taken in conjunction with the accompanying drawings which show by way of example preferred embodiments of the invention.

DESCRIPTION OF PREFERRED EMBODIMENTS

Now, the invention is described more particularly by way of its preferred embodiments with reference to the accompanying drawings.

Figure 1:
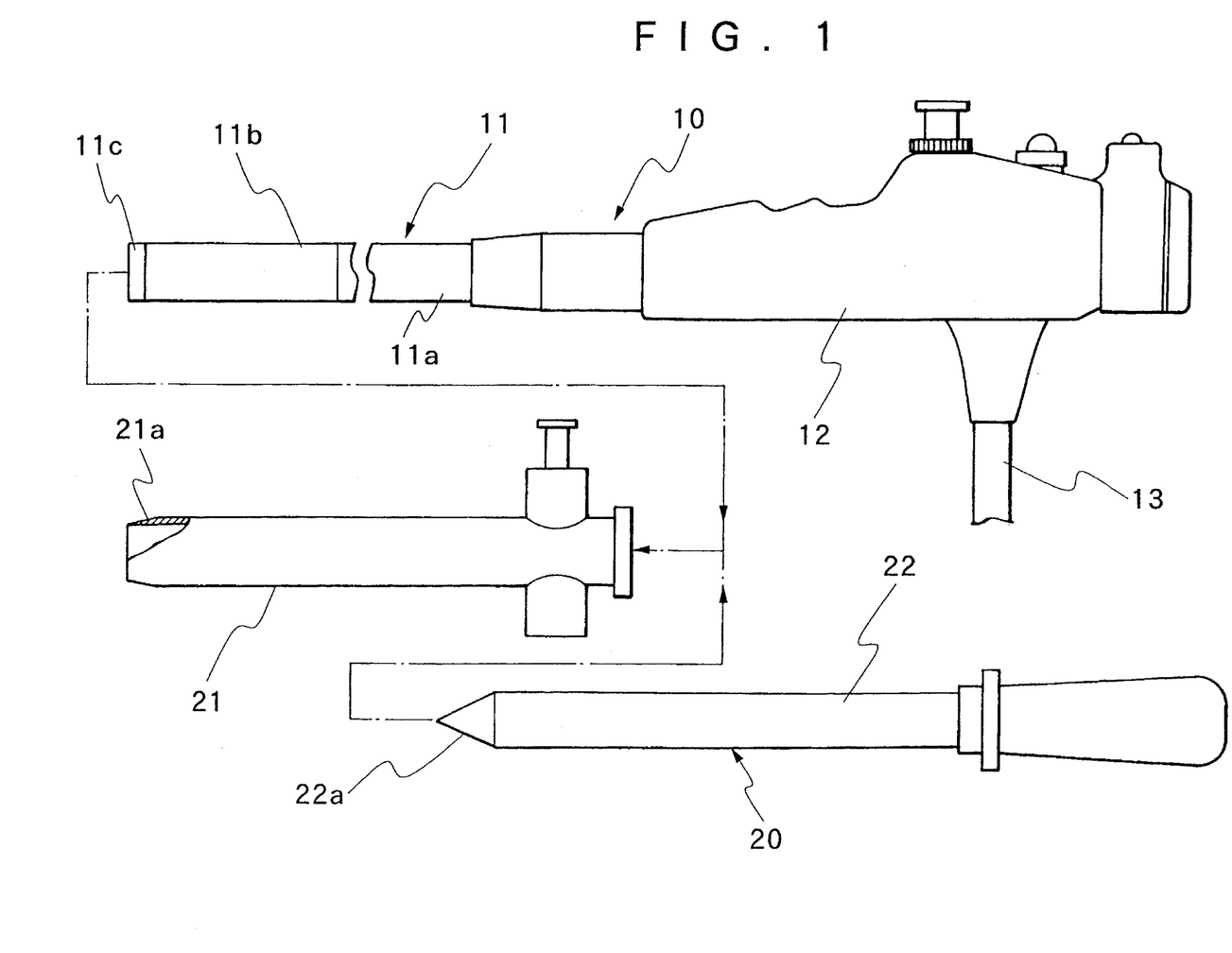
FIG. 1 is schematic outer views of an endoscope and a trocar.

Shown schematically in FIG. 1 are an endoscope and a trocar to be used as a guide for the endoscope. In FIG. 1, the reference numeral 10 indicates an endoscope which is largely constituted by an insertion rod 11 to be introduced into an intracavitary portion, and a manipulating head assembly 12 which is connected to the proximal end of the insertion rod 11. This particular endoscope 10 is built as an electronic endoscope which is arranged to convert images of an intracavitary portion under observation into electric signals through a photoelectric image sensor and to display its video images on a monitor screen on the basis of signals form the image sensor. For this purpose, led out of the manipulating head assembly 12 is a universal cable 13 which contains a light guide cable and a signal cable to be connected to a signal processor.

Denoted at 20 is a trocar which is composed of an outer sheath member 21 and an inner perforator needle 22 with a sharp-pointed end 22a. In use, the perforator needle 22 is put into the outer sheath member 21 so that its sharp-pointed end 22a is projected out of the fore end of the outer sheath member 21. The outer sheath member 21 is forwardly tapered or thinned down in its fore end portion in the fashion of a knife edge as indicated at 21a to eliminate radially stepped surfaces from the profile of the trocar 20. With the perforator needle 22 set in the outer sheath member 21 in this manner, the trocar 20 is introduced into the body of patient to a predetermined depth depending upon the location of an intracavitary portion of interest, by piercing through outer skin layers of the body with the sharp-pointed end 22a of the perforator needle 22. Thereafter, the inner perforator needle 22 is extracted from the outer sheath member 21, and instead the insertion rod 11 of the endoscope 10 is introduced into the intracavitary region through the outer sheath member 21 of the trocar 20 for an endoscopic examination or for other purposes, Both of the outer sheath member 21 and the inner perforator needle 22 of the trocar 20, which guides the endoscopic insertion rod 11, are made of a hard rigid material. Nevertheless, in most case there arises a necessity for turning the tip end of the endoscopic insertion rod 11 in the trocar 20 toward a direction of particular interest. For this purpose, the endoscopic insertion rod 11 is provided with a flexibly bendable angle section 11b contiguously between a main insertion rod section 11a, which determines the length of the insertion rod 11, and a rigid tip end section 11c which supports endoscopic observation means at the tip end of the insertion rod 11. The angle section 11b is constituted by a plural number of angle rings 30 which are pivotally connected one after another to provide a flexible structure. The angle rings 30 are wrapped in fine wire mesh 31 which serves as a substrate layer for an outer resilient skin layer 32 of soft and resilient material such as urethane resin or the like (FIG. 2).

Figure 2:
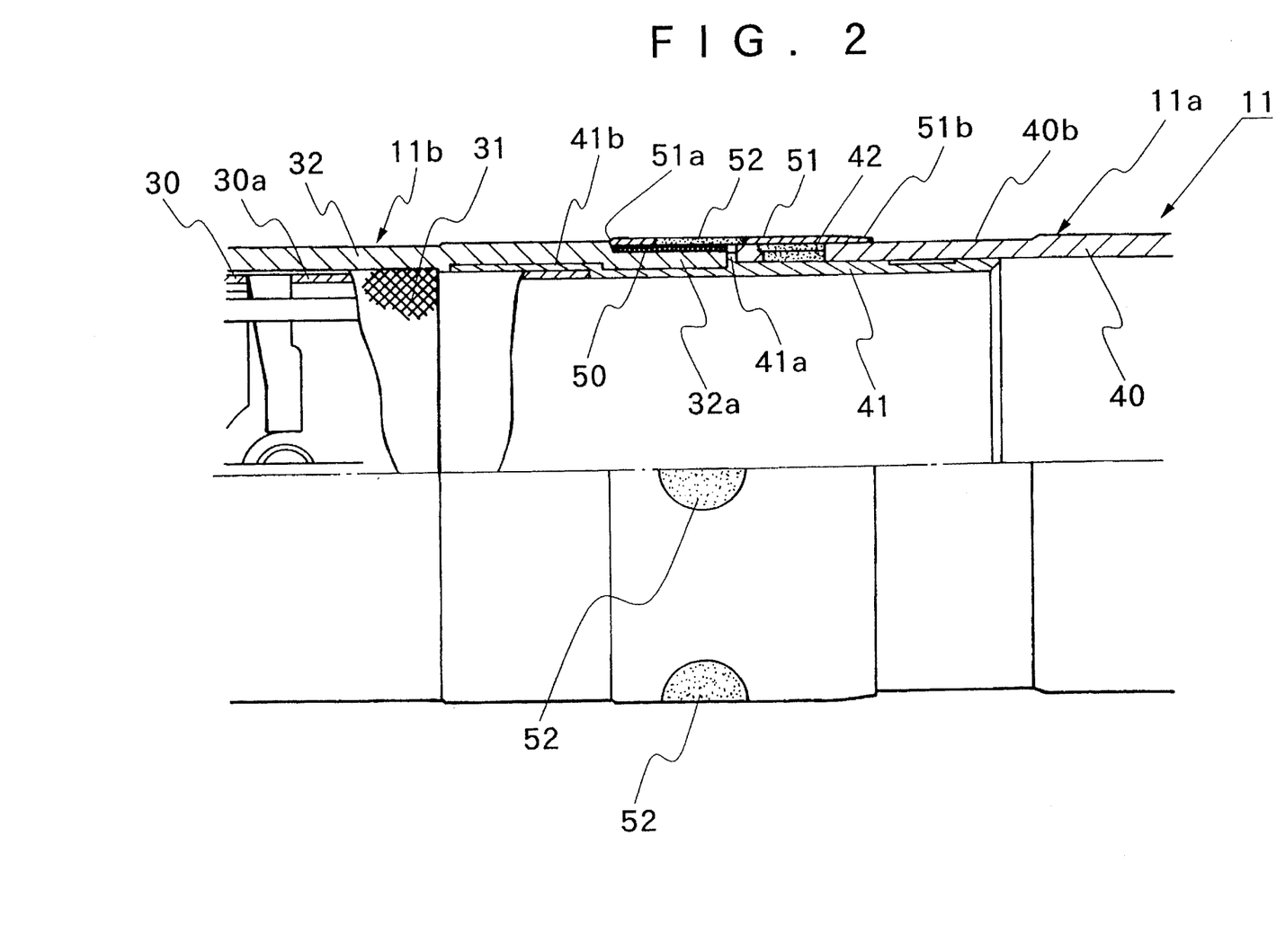
FIG. 2 is a schematic sectional view of a joint between an angle section of an endoscopic insertion rod and a main insertion rod section.
Figure 3:
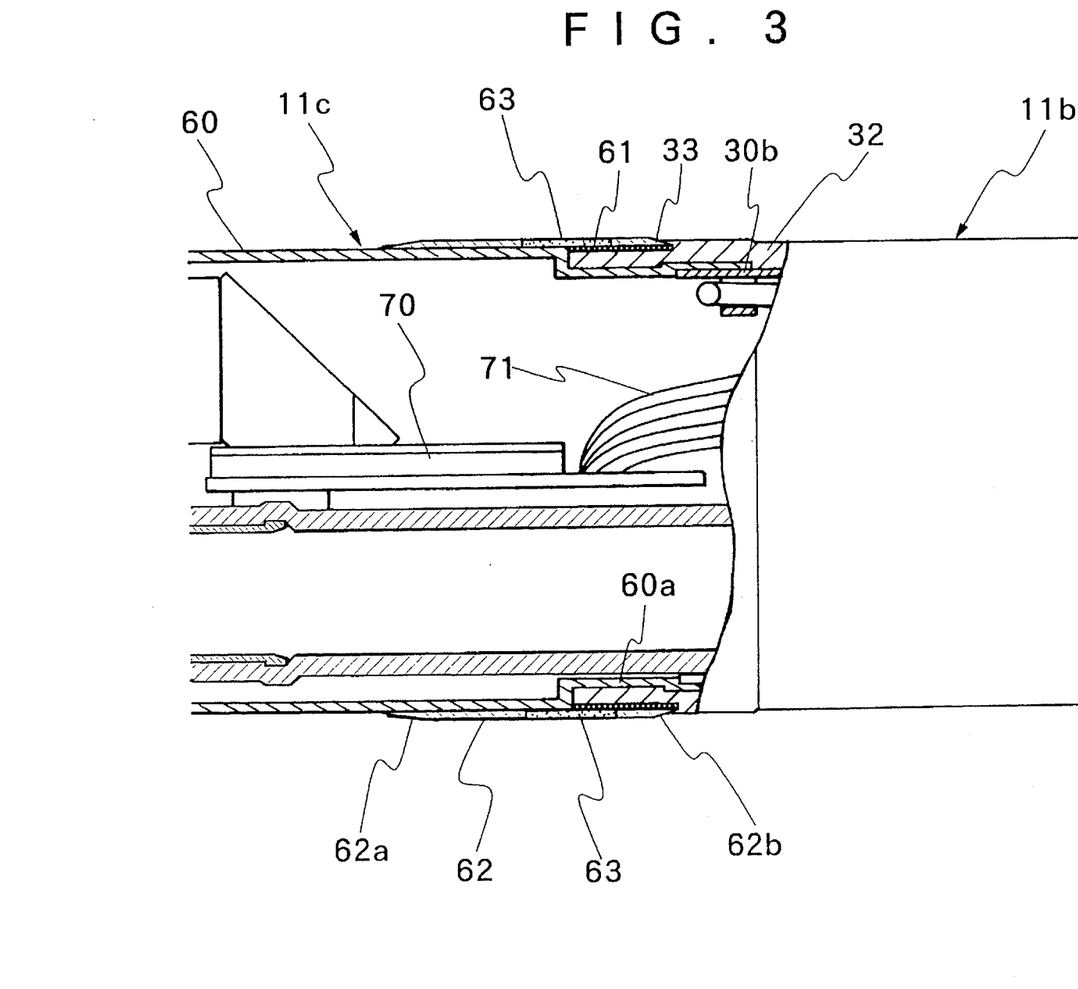
FIG. 3 is a schematic sectional view of a joint between an angle section and a rigid tip end section of an endoscopic insertion rod, incorporating the joint construction according to the invention.

Referring to FIGS. 2 and 3, there are shown a joint construction connecting the proximal end of the angle section 11 with the main insertion rod section 11a, and a joint construction connecting the fore end of the angle section 11b with the rigid tip end section 11c, respectively. In this particular embodiment, the joint construction according to the invention is embodied into the joint between the angle section 11b and the rigid tip end section 11c of the endoscopic insertion rod 11.

More particularly, shown in FIG. 2 is a joint construction connecting the angle section 11b with the main insertion rod section 11a of the endoscope. The main insertion rod section 11a includes a tubular body 40 which is constituted by a rigid metal pipe or the like and, although not shown particularly in the drawings, accommodates a light guide, an electric signal cable, a biopsy channel and so forth. A coupling ring 41 is fitted into a fore end portion of the tubular body 40 of the main insertion rod section 11a until the fore end face of the tubular body 40 comes into abutment against a stopper ridge 41a which is provided on the outer periphery of the coupling ring 41 substantially centrally of the axial length thereof. On the other side of the stopper ridge 41a or on the side away from the tubular body 40, the coupling ring 41 is centrally provided with a stepped portion on its outer periphery, defining a larger diameter portion 41b on the front side of a sunken smaller diameter portion. The fore end portion of the tubular body 40, which is in fitting engagement with the coupling ring 40, is bored with a number of perforations 42 which are filled with a solder for securely fixing the coupling ring 41 to the tubular body 40 of the main insertion rod section 11a.

Of the angle rings 30 which constitute the angle section 11b, an angle ring 30a in the proximal end position is fitted in and fixed in position within the larger diameter portion of the coupling ring 41 by the use of an adhesive or other suitable fixation means. The mesh 31 is extended to a position short of the coupling ring 41, but the outer skin layer 32 is extended onto the coupling ring 41 for abutment against the stopper ridge 41a at its proximal end.

The resilient outer skin layer 32 is provided with a reduced diameter portion 32a at its proximal end, which is firmly fastened against the sunken surface of the coupling ring 41 by a line-wrapping 50 layer. A rigid metallic cover ring 51 of stainless steel or the like is fitted on the line-wrapping layer 50 to hold the latter in position on the coupling ring 41. Similarly to the rigid cover ring 6 shown in FIG. 6, the rigid cover ring 51 is externally gradually tapered or thinned down in its opposite end portions to provide external bevel surfaces 51a and 51b, which join the surfaces of the outer skin layer 32 and the tubular body 40 of the main insertion rod section 11a through a smooth streamlined contour line free of radially stepped surfaces. Before bonding the rigid cover ring 51 in position on the line-wrapping layer 50, it can be slid to and from a receded position on the tubular body 40 of the main insertion rod section 11a, that is, to and from a reduced diameter portion 40a which is provided at the fore end of the tubular body 40. In order to permit the sliding displacements of the rigid cover ring 51, the reduced diameter portion 40a is formed over a predetermined length from the fore distal end of the tubular body 40 and in an outside diameter which is sunken from the rest of the tubular body 40 to an extent corresponding to the thickness of the rigid cover ring 51. Further, the rigid cover ring 51 is provided with a number of adhesive feed apertures 52 at intervals around the girder thereof.

On the other hand, at the junction between the angle section 11b and the rigid tip end section 11c, a reduced diameter portion 60a is provided at the proximal end of a tubular member 60, as seen in FIG. 3, the tubular member 60 being extended from a main body (not shown) of the rigid tip end section 11c, which is equipped with illumination and observation windows for the endoscope. The reduced diameter portion 60a is fitted on an angle ring 30b in the foremost position of the angle section 11b and fixed in position by the use of an adhesive, solder or other suitable fixation means. The fore end of the afore-mentioned outer skin layer 32 of the angle section 11b is fitted on the reduced diameter portion 60b, and firmly fastened in position by a line-wrapping layer 61. A rigid cover ring 62 is fitted and fixed on the line-wrapping layer 61. The rigid cover ring 62 is also provided with a number of adhesive feed apertures 63 at intervals around the Girder thereof. The respective apertures 63 are filled with an adhesive at the time of fixation of the rigid ring 62.

Figure 4:
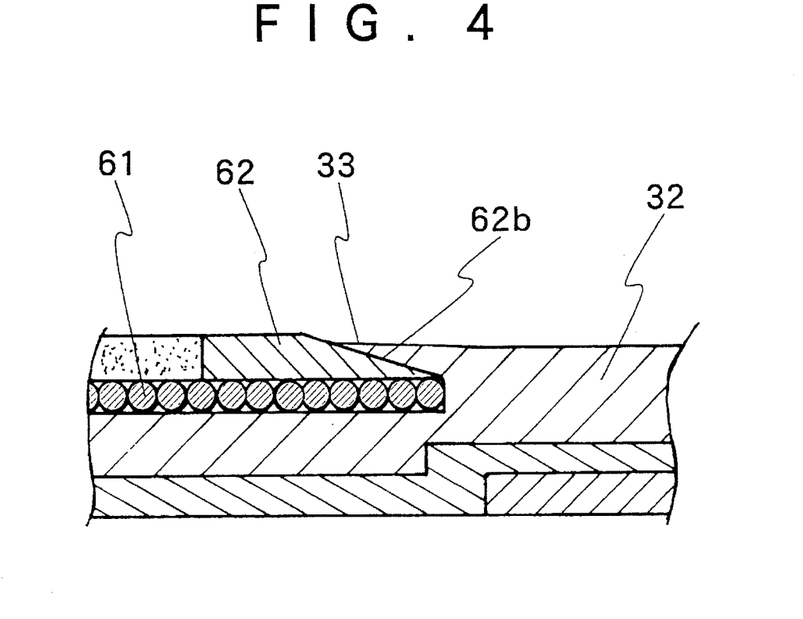
FIG. 4 is an enlarged fragmentary sectional view of a rigid cover ring partly embedded in an outer skin layer.

Similarly to the rigid cover ring 51 at the Joint between the angle section 11b and the insertion rod section 11a, the rigid cover ring 62 is externally gradually tapered or thinned down in its opposite end portions to provide external bevel surfaces 62a and 62b. In this case, the bevel surface 62a on the rigid cover ring 62 is located on the tubular member 60, of a rigid metal pipe or the like, of the rigid tip end section 11c, while the other bevel surface 62b is extended onto the outer skin layer 32 of the angle section 11b. The outer skin layer 32 is provided with a forwardly tapered annular fin 33 on the border of the sunken surface on which the line-wrapping layer 61 is formed. The annular fin 33 is Gradually thinned down toward its outer end in a blade-like shape in section, defining a bevel surface on the inner side complementarily to or substantially at the same angle as the external bevel surface 62b on the rigid cover ring 62. The annular fin 33 is securely fixed on the external bevel surface 62b of the rigid cover ring 62 by the use of an adhesive. The width or the axial extension length of the internal bevel surface on the annular fin 33 is preferably slightly shorter than the axial length of the external bevel surface 62*a*, so that it covers the external bevel surface 62*a* up to a point a little below the top surface of the rigid cover ring 62 without extending onto the circumferential surface of the latter.

The first rigid cover ring 51 is slidable along the tubular body 40 of the main insertion rod section 11*a* toward and away from one end of the outer skin layer of the angle section 11*b* while the second rigid cover ring 62 is slidable along the tubular member 60 of the fore tip end section 11*c* toward and away from the other end of the outer skin layer 32. Therefore, while forming the line-wrapping layers 50 and 61 on the opposite end portions of the outer skin layer 32 of the angle section, the rigid cover rings can be retained in a receded position on the tubular body 40 or 60, and, once the line-wrapping layers 50 and 61 are formed, they can be slid onto the respective positions on the line-wrapping layers 51 and 60 and fixed in position by application of an adhesive into the apertures 52 and 63 in the bodies of the rigid cover rings 51 and 62, respectively. At this time, excess adhesive should not bulges out on the circumference of each rigid cover ring. Further, the bevel surface 62*b* on the rigid cover ring 62 is embedded under the annular fin 33 of the resilient outer skin layer 32, which has its internal bevel surface securely bonded to the bevel surface 62*b* by the use of an adhesive.

With the above-described arrangements, at the time of an endoscopic examination of an abdominal cavity, for instance, the endoscopic insertion rod 11 is introduced into the sheath member 21 of the trocar in place of the perforator needle 22. In addition to insertion and extraction into and out of the sheath member 21 of the trocar, the endoscopic insertion rod is usually moved back and forth within the sheath member 21 for adjustments of the position of endoscopic observation means at the tip end of the insertion rod for examination of a particular region in the abdominal cavity, sliding the insertion rod section 11*a* and angle section 11*b* along the inner surfaces of the outer sheath member 21. On such occasions, the rigid cover ring 62 on the line-wrapping layer 50, which holds the proximal end of the outer skin layer of the angle section 11*b* at the joint with the insertion rod section 11*b*, prevents direct contact of the line-wrapping layer 50 with the sharp-edged tapered end portion 21*a* at the fore end of the outer sheath member 21.

In order to manipulate the endoscopic observation means within an abdominal cavity, the rigid tip end section 11*c* at the distal end of the insertion rod 11 as well as the angle section 11*b* need to be entirely protruded out of the outer sheath member 21. For this purpose, it is necessary to protrude the angle section 11*b* of the insertion rod 11 completely out of the sharp-edged fore end of the outer sheath 21, including the rigid cover rings 51 and 62 at the rear and front ends of the angle section 11*b*. As long as a forward movement is concerned, the rigid cover rings 51 and 62 on the insertion rod 11 can be protruded out of the sheath member 21 without meeting any obstacle since the sharp edges of the tapered end portion 21*a* lie in the same direction as the movement of the insertion rod 11.

However, at the time of withdrawing the insertion rod 11 from the sheath member 21 of the trocar, the edges of its tapered portion 21 would normally tend to oppose firstly against re-entry of the rigid cover ring 51 which is provided at the joint of the angle section 11*b* with the fore end of the main insertion rod section 11*a*. At this time, however, the fore end edges of the sheath member 21 are permitted to ride onto the rigid cover ring 51 easily along the external bevel surface 51*a* at the proximal end of the rigid cover ring 51 which is tightly fitted on the tubular body 40 of the main insertion rod section 11*a*, which is likewise a rigid structure, without forming a radially stepped surface which would hinder withdrawal of the insertion rod 11 by abutment against the sharp-edged fore end of the sheath member 21. Accordingly, after riding over the rigid cover ring 51, the tapered end 21*a* of the sheath member 21 is slid along the outer skin layer 32 of the angle section 11*b* toward the proximal end of the other rigid cover ring 62 at the joint with the rigid tip end section 11*c* of the insertion rod 11.

Since the bevel surface 62*b* at the proximal end of the rigid cover ring 62 is embedded under the annular fin 33 of the resilient outer skin layer 32, the tapered end 21*a* of the sheath member 21 is slid across the fin 33 to ride onto the rigid cover ring 62 without directly contacting the edges of the ring 62. After completely riding over the rigid cover ring 62, the tapered end 21*a* is slid along the outer surface of the rigid tip end section 11*c* as the endoscopic insertion rod 11 is further retracted into the sheath member 21 for extraction from the trocar.

As clear from the foregoing description, the bevel surface 62*b* of the rigid cover ring 62 is embedded under the annular lip portion 33 rising to the top of the ring 62 continuously and smoothly from the outer skin layer 32, so that the tapered fore end 21*a* of the sheath member 21 can be smoothly displaced onto the rigid cover ring 62 at the time of extraction of the insertion rod 11.

In the particular embodiment shown in the drawings, it is not necessarily required to provide an annular fin bordering on the bevel surface 62*a* at the other end of the rigid cover ring 62 or on any of the bevel surfaces 51*a* and 51*b* of the other rigid cover ring 51. This is because edges of the forwardly tapered bevel surfaces 62*a* and 51*a*, which are disposed forwardly in the direction of insertion of the endoscope, have no possibilities of coming into abutting engagement with the sharp-edged fore end 21*a* of the sheath member 21 from the opposite direction at the time of extraction of the endoscope. On the other hand, the bevel surface 51*b* at the proximal end of the rigid cover ring 51, which opposingly meets the tapered fore end 21*a* of the sheath member 21 at the time of extraction of the endoscopic insertion rod 11, should be free of a radially stepped surface as would hinder the extraction of the insertion rod by abutting against the sharp-edged tapered end 21*a* of the sheath member 21. However, in the particular embodiment shown, the bevel surface 51*b* is located and tightly fitted directly on a skinless surface of the rigid tubular body 40 in such a manner as to form a substantially stepless streamlined profile continuously from the main insertion rod section 11*a*. This arrangement is good for hard endoscopes which have an insertion rod body of a rigid pipe. However, in case of a flexible endoscope with a flexible insertion rod section with a resilient outer skin layer, the bevel surface 51*a* of the rigid cover ring 51 at the joint with the flexible insertion rod section should also be embedded and fixedly anchored under a similar annular fin which is formed in the outer skin layer at a position bordering on the outer edges of the bevel surface 51*a*.

In this instance, as mentioned hereinbefore, the annular fin 33 is preferably extended slightly short of the top end of the bevel surface 62*b* on the rigid cover ring 62 for the purpose of preventing top end portions of the annular fin 33 from being scraped off by contact with the sharp-edged fore end of the trocar sheath member as the latter is caused to ride over the rigid cover ring 62 repeatedly by back and forth movements of the endoscopic insertion rod within the sheath member. However, if desired, the annular fin 33 may be arranged to cover substantially the entire bevel surface 62b in case the fin 33 can be bonded securely to the latter.

As clear from the particular embodiments described above, the present invention provides an improved joint construction for connecting a bending angle section of an endoscopic insertion rod between preceding and succeeding sections of an endoscopic insertion rod, the joint construction including a line-wrapping layer formed around an end portion of a resilient outer skin layer of the angle section and firmly fastening same to an underlying rigid structure at a joint with one of the preceding and succeeding sections of the insertion rod, a rigid cover ring fixedly fitted on the line-wrapping layer and provided with outwardly tapered external bevel surfaces at the opposite ends thereof, and a forwardly tapered annular fin formed in and out of the resilient outer skin layer at a position bordering on outer edges of an external bevel surface at the proximal end of the rigid cover ring, the annular fin being overlaid and securely bonded to the external bevel surface, embedding the external bevel surface at the proximal end of the rigid cover ring under the resilient outer skin layer. Accordingly, the line-wrapping layer which is anchored in position by the use of an adhesive has no possibility of being exposed to the outside. In addition, the proximal end face of the rigid cover ring on the line-wrapping layer is completely kept from abutting engagement with the sharp-edged fore end of the sheath member of a trocar, ensuring smooth movements of the endoscopic insertion rod at the time of introduction and extraction into and out of a trocar.

What is claimed is:

1. A joint construction for connecting a flexibly bendable angle section of an endoscopic insertion rod to an anteriorly or posteriorly adjoining section of said endoscopic insertion rod, including a line-wrapping layer tightly fastening an end of a resilient outer skin layer of an angle section against an underlying rigid structure at a joint with an adjoining section of an insertion rod, and a rigid cover ring fixedly fitted on said line-wrapping layer for protection thereof, characterized in that said joint construction comprises:

front and rear external bevel surfaces formed at front and rear ends of said rigid cover ring, respectively, by externally tapering front and rear end portions of said rigid cover ring; and a forwardly tapered annular fin formed in and out of a resilient outer skin layer under said rigid cover ring at a position bordering on outer edges of said rear external bevel surface of said rigid cover ring and having an internal bevel surface complementarily to said rear external bevel surface on said rigid cover ring, said internal bevel surface of said annular fin being securely bonded on said rear external bevel surface of said rigid cover ring, embedding said rear external bevel surface under said resilient outer skin layer.

2. A joint construction as defined in claim 1, wherein said annular fin is arranged to cover said rear external bevel surface of said rigid cover ring up to a point a little short of a top end of said rear bevel surface.

3. A joint construction as defined in claim 1, wherein said rigid cover ring is fitted on a line-wrapping layer formed on a fore end portion of a resilient outer skin layer of an angle section at a joint with an anteriorly located rigid tip end section of an endoscopic insertion rod, and said annular fin is formed in and out of said outer skin layer of said angle section at a position bordering on outer edges of said rear bevel surface of said rigid covering thereby to embed said rear bevel surface under said outer skin layer of an angle section.

4. A joint construction as defined in claim 3, wherein a foremost angle ring of an angle section is connected to a tubular rigid body of an rigid tip end section, and said rigid cover ring is slidable into a receded position on said tubular rigid body of an section while forming said line-wrapping layer on said resilient outer skin layer of an angle section.

5. A joint construction as defined in claim 1, wherein said rigid cover ring is fitted on a line-wrapping layer formed on a fore end portion of a resilient outer skin layer of a main insertion rod section posteriorly adjoining an angle section, and said annular fin is formed in and out of said outer skin layer of an angle section at a position bordering on outer edges of said rear bevel surface of said rigid covering thereby to embed said rear bevel surface under said outer skin layer of an main insertion rod section.

* * * * *